United States Patent
Pillai et al.

(10) Patent No.: US 6,733,177 B2
(45) Date of Patent: May 11, 2004

(54) FRICTION RING FOR IMPROVED ORBITAL BALANCE OF C-ARM X-RAY APPARATUS

(75) Inventors: Vipin J. Pillai, Bangalore (IN); Sourav Ghosh, Bangalore (IN)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 0 days.

(21) Appl. No.: 10/242,023

(22) Filed: Sep. 12, 2002

(65) Prior Publication Data

US 2004/0052334 A1 Mar. 18, 2004

(51) Int. Cl.[7] .............................. H05G 1/02; F16D 51/00
(52) U.S. Cl. ...................... 378/198; 378/193; 378/197; 188/77 W
(58) Field of Search .................................. 378/193, 194, 378/195, 196, 197, 198; 188/77 W

(56) References Cited

U.S. PATENT DOCUMENTS

| | | | | |
|---|---|---|---|---|
| 4,955,046 A | * | 9/1990 | Siczek et al. | 378/197 |
| 5,073,917 A | * | 12/1991 | Van Endschot et al. | 378/197 |
| 5,499,284 A | * | 3/1996 | Pellegrino et al. | 378/198 |
| 5,521,957 A | * | 5/1996 | Hansen | 378/198 |
| 5,921,355 A | * | 7/1999 | Mostrom | 188/77 W |
| 6,113,265 A | * | 9/2000 | Babler | 378/197 |
| 6,609,826 B1 | * | 8/2003 | Fujii et al. | 378/198 |

* cited by examiner

*Primary Examiner*—Edward J. Glick
*Assistant Examiner*—Allen C. Ho
(74) *Attorney, Agent, or Firm*—Joseph S. Heino; Carl B. Horton

(57) ABSTRACT

A variable friction disc brake for use with a C-arm x-ray imaging apparatus interposed between the support arm and yoke of the imaging apparatus. The variable friction disc is generally comprised of ring having a gap, width both sides of said gap having apertures therethrough such that a bolt may be inserted into said apertures and used to adjust the width of the gap, and the tension on the ring.

20 Claims, 5 Drawing Sheets

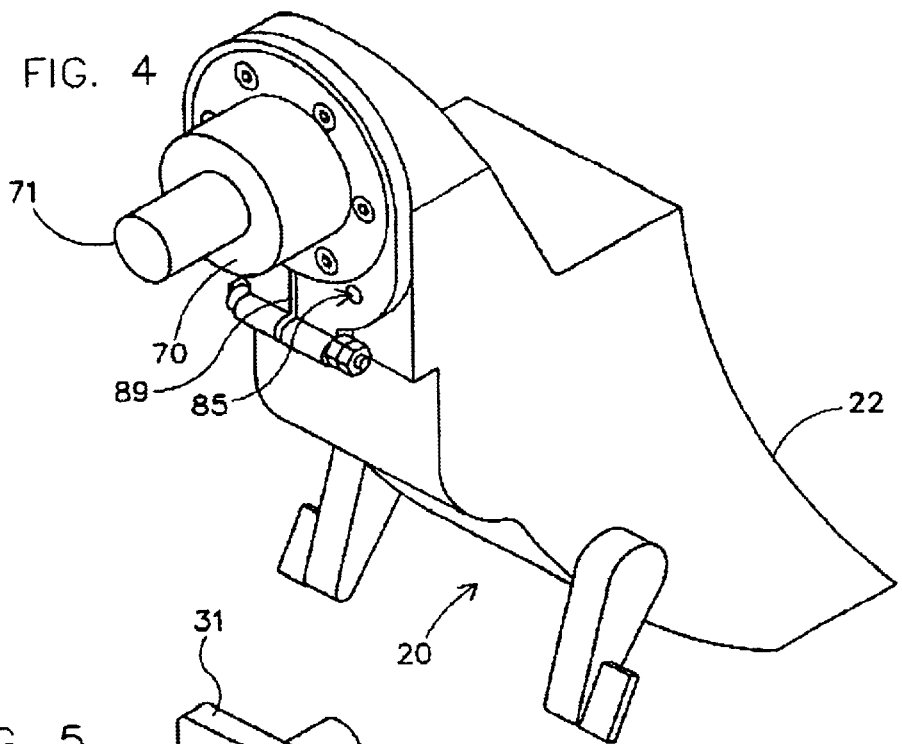
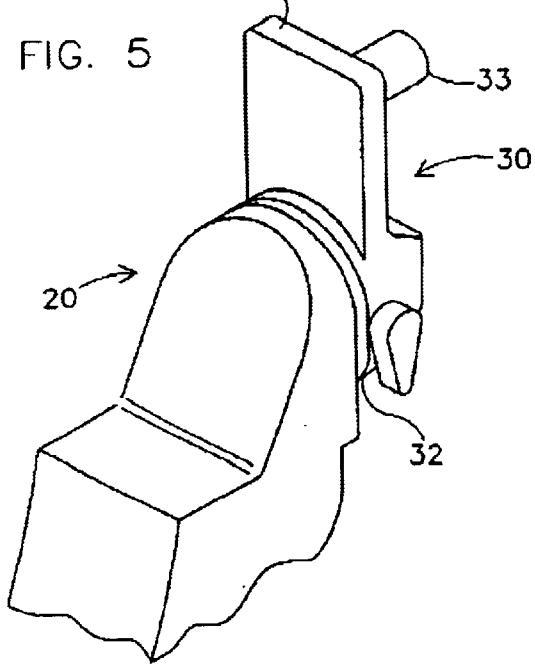

FRICTION RING FOR IMPROVED ORBITAL BALANCE OF C-ARM X-RAY APPARATUS

BACKGROUND OF THE INVENTION

1. Field of the Invention

The present invention relates generally to the area of x-ray imaging systems and devices used with such diagnostic x-ray systems. More specifically, the present invention relates to a C-arm x-ray imaging apparatus that incorporates new and improved mechanisms for adjustment and control of the C-arm during usage.

2. Background of the Invention

It is frequently desired to conduct an x-ray examination of a patient by positioning the x-ray equipment such that a number of different views of the area of interest, and from several different positions, may be obtained. It is also preferable to do so without the need to reposition the patient. Mobile C-arm x-ray diagnostic equipment, such as that shown in FIGS. 4A and 4B of the present application, has been developed to meet these needs and is now well known in the medical and surgical arts. The C-arm x-ray machine is especially useful in that it is small enough and mobile enough to be present in an operating or exam situation without requiring the physician to repeatedly move or requiring the patient to change positions to obtain suitable radiographic images.

C-arm imaging systems are widely used in the medical arts. Examples of their uses include bone density measurement and fluoroscopic imaging during surgical procedures. The term "C-arm" refers to the generally C-shaped member that has an x-ray source and an image receptor, or detector, mounted on opposing ends of the C-arm. In this fashion, x-rays emitted by the source are incident on and detected by the detector. The x-ray source and the detector are positioned such that when, for example, a human extremity is interposed between the x-ray source and the image receptor, thereby exposing the extremity to x-ray radiation, the receptor produces data representative of characteristics of the interposed extremity. The data produced may be displayed on a monitor and electronically saved.

The C-arm portion of the machine is normally mounted such that it is permitted two degrees of freedom. First, the C-arm track is slidably mounted to a C-arm support member so as to be movable in relation to the support member. This permits the x-ray source and image receptor to be moved rotatably about the arc of curvature of the track in the C-arm. Second, the C-arm support member permits rotation of the C-arm about its axis. Often the support member is in the general shape of an L and may be referred to as the yoke. Mobile C-arms have a third degree of freedom in that they are free to move in a plane that is horizontally parallel to the floor and a fourth in that the C-arm can be raised and lowered.

Obviously, a support structure that permits rotation and movement of such a C-arm must be constructed to withstand very large torsional, tensile and compressive stresses and moments. It must also be constructed so as to provide a support structure that is heavy enough and a center of gravity that is low enough to avoid imbalance and tipping of the machine when the C-arm and Yoke are rotated or raised, which in some cases causes a dramatic shift in the center of mass of the equipment.

Additionally, C-arm x-ray equipment must be delicately positioned in order to render the image or images desired by the physician. Unfortunately, the weight of the support structure makes it difficult to position the C-arm. Therefore, it is desirable to design a source of frictional drag between the C-arm and the support member as well as on the C-arm track to assist with this positioning.

It is also desirable to balance the C-arm, x-ray source, x-ray detector and Yoke so that relatively little physical effort is required to move the C-arm about the orbital rotation axis and the lateral rotation axis. One manner of accomplishing this is to design the C-arm such that its center of mass is as close as possible to the orbital and lateral rotation axes.

Some C-arm designs require a center of mass that is separate and apart from the axis of rotation. In these unbalanced designs, the user must exert significant force to rotate the apparatus. This physical exertion generally detracts from other, more significant tasks a health care provider may be undertaking. Also, unbalanced designs can be dangerous to both the operator and the patient. For example, unbalanced C-arms require much more powerful braking systems. Without a braking system, the C-arm could rotate downwardly and forceably strike a patient during positioning or during examination. Unfortunately, a completely balanced C-arm x-ray imaging system is nearly impossible to design due to variances in manufacturing.

BRIEF SUMMARY OF THE INVENTION

It is therefore an object of the present invention to provide a C-arm x-ray apparatus that is either optimally balanced or that requires little effort to rotate. It is yet another object of the present invention to provide such a device that requires relatively few parts and that can be easily manufactured. It is also an object of the present invention is to increase the friction between the C-arm and the Yoke so as to improve rotational control of the C-arm when the brake is not applied. Yet another object of this invention is to provide such a device while not increasing the overall length of the C-arm machine, which increase in length would also serve to decrease overall stability of the machine. It is yet another object of the present invention to provide an aesthetically pleasing and aseptic device.

The present invention has obtained these objects. It employs a device to control the rotation of the C-arm when the physician or health care provider is adjusting the C-arm machine to ready it for examination purposes. Additional objects and advantages of the invention will be set forth in the description that follows. Other objects and advantages may be learned by practice of the invention.

BRIEF DESCRIPTION OF THE DRAWINGS

FIG. 4 is a top, rear and left side perspective view of the frictional brake element as installed on a yoke of the type employed in the present invention.

FIG. 5 is a top, front and right side perspective view of the yoke and support arm of the type employed in the device of the present invention.

DETAILED DESCRIPTION OF THE INVENTION

The following detailed description is intended to describe the preferred embodiments that are depicted in the figures. It is to be understood that changes could be made to that which is specifically described and shown that would still fall within the scope of the present invention.

Figure 1A:
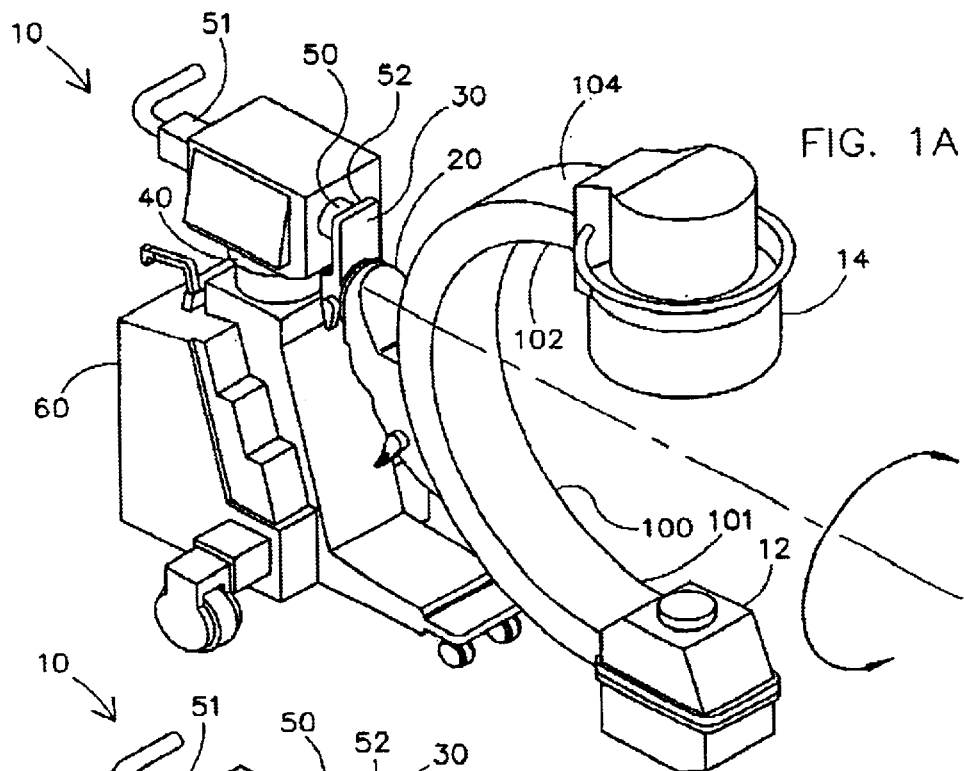
FIG. 1A is top, front, and left side perspective view of a C-arm x-ray machine and showing the C-arm in a nearly vertical position, the x-ray receptor being positioned immediately above the source.
Figure 1B:
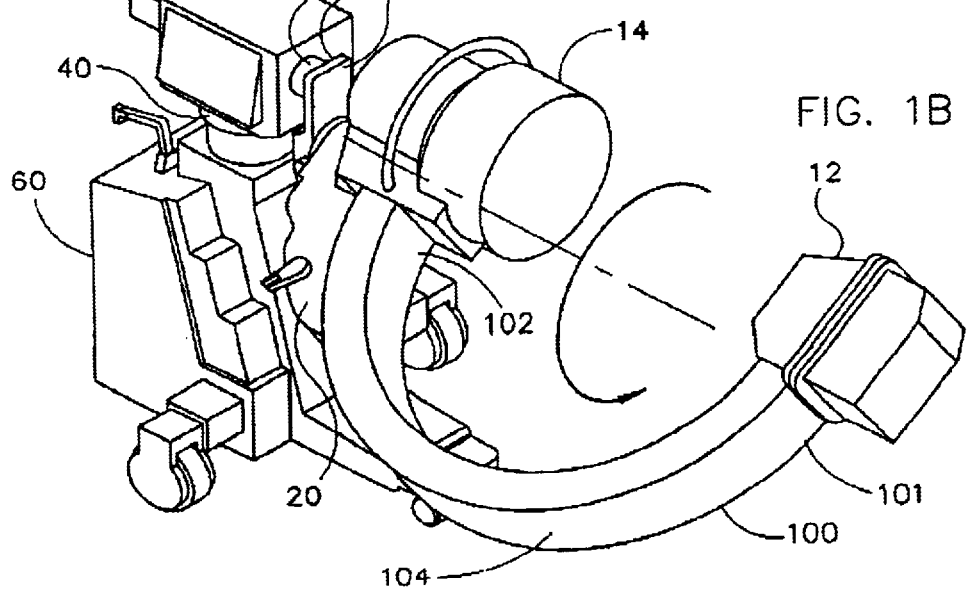
FIG. 1B is another top, front, and left side perspective view of the C-arm x-ray machine illustrated in FIG. 1A but showing the C-arm in a more horizontal position and the x-ray source being rotated fully downwardly.

Referring now to the drawings in detail, wherein like numbered elements refer to like elements throughout, FIGS. 1A and 1B depict the basic components of an imaging system such as that used in the present invention. In general, a C-arm x-ray imaging machine, generally identified 10, is comprised of the following components: an x-ray source 12, an image receptor 14, an image processing system, a display and viewing system, a high voltage generator and a control unit. In application, an imaging object (not shown) would be interposed between the x-ray source 12 and the receptor 14.

The x-ray source 12 preferably comprises an x-ray tube and a high-voltage generator. The high-voltage generator is connected to an adjustable high-voltage power supply capable of generating approximately −70 kV to −120 kV. When the machine 10 is operated, the charged particle beam strikes the target and generates x-ray photons. The x-ray photons pass through a collimator and form an x-ray beam. The x-ray beam has an axis that is substantially aligned with the center of the active area of the x-ray detector 14. The x-ray beam has a vector that is defined by the axis of the x-ray beam in the direction of the x-ray detector assembly 14.

The imaging object generally refers to the patient X-rays that have passed through the patient are detected and later processed and studied for some form of interpretation.

The detection and recording system is generally comprised of the image receptor 14. The image receptor 14 captures the x-ray photons scanned across the imaging object and converts them to electrical signals. The impulses are then converted to digital data and either stored or fed immediately into a computer for image reconstruction. The imaging process system generally consists of a computer with a software package that reconstructs the image and displays the image on a screen and a device that provides for storage of the image.

The display system and the control unit are normally remotely, operated. Thus the operator can be shielded from radiation while still performing the x-ray study. Alternatively, the entire system can be placed in an examining or operating room so that the health care provider can view images of the patient in real time.

The mobile c-arm x-ray imaging machine, generally identified 10, is comprised of a wheeled support base 60. In a preferred embodiment, the support base 60 is a generally rectangular upright body that may be equipped with one or more video monitors and has an upper portion or vertically extendable column 40 with an extendable cross arm 50. The extendable cross arm 50 has a first portion 51 slidably mounted within the vertically extendable column 40 and a second end 52 having an aperture 54 actually in the end of the cross arm 50. The support base 60 is important to the imaging system 10 in that it provides a platform for the support arm 30, yoke 20 and C-arm 100. Therefore, the support base 60 should have a footprint large enough such that the yoke 20 and C-arm 100 are permitted to rotate without the danger of tipping and/or the support base 60 must be heavy enough to prevent tipping of the x-ray apparatus 10.

The device of the present invention, unlike previous devices, provides a support arm 30 between the yoke 20 and the support base 60. The support arm 30 is designed to lower the axis of rotation such that the axis of rotation coincides, or very nearly coincides, with the center of gravity of the C-arm 100. The closer the center of gravity of the C-arm 100 to its axis of rotation, the smaller the force required to rotate the C-arm 100.

The support arm 30 is a generally rectangular part having a first end 31 with a support pin 33 that is insertable into the second end 52 of the cross arm 50 and a thick second end 32 offering an aperture 34 that accommodates the pin 23 and steel sleeve 70 of the yoke 20. The support pin 33 is set at a slightly upward angle to compensate for the weight of the C-arm 100 and yoke 20. See also FIGS. 2, 3 and 5.

The yoke 20 is attached at its first end 21 to the support arm 30 and at its second end 22 to the C-arm 100. Obviously, the yoke 20 must be able to withstand a wide variance in forces not only as the C-arm 100 is moved along the yoke 20, but as the C-arm 100 is rotated. Additionally, the yoke 20 must be an item of relatively low weight despite design guidelines requiring a relatively high factor of safety. Low weight is a requirement for the design so that the C-arm 100 can be easily repositioned during an examination.

Figures 2, 3:
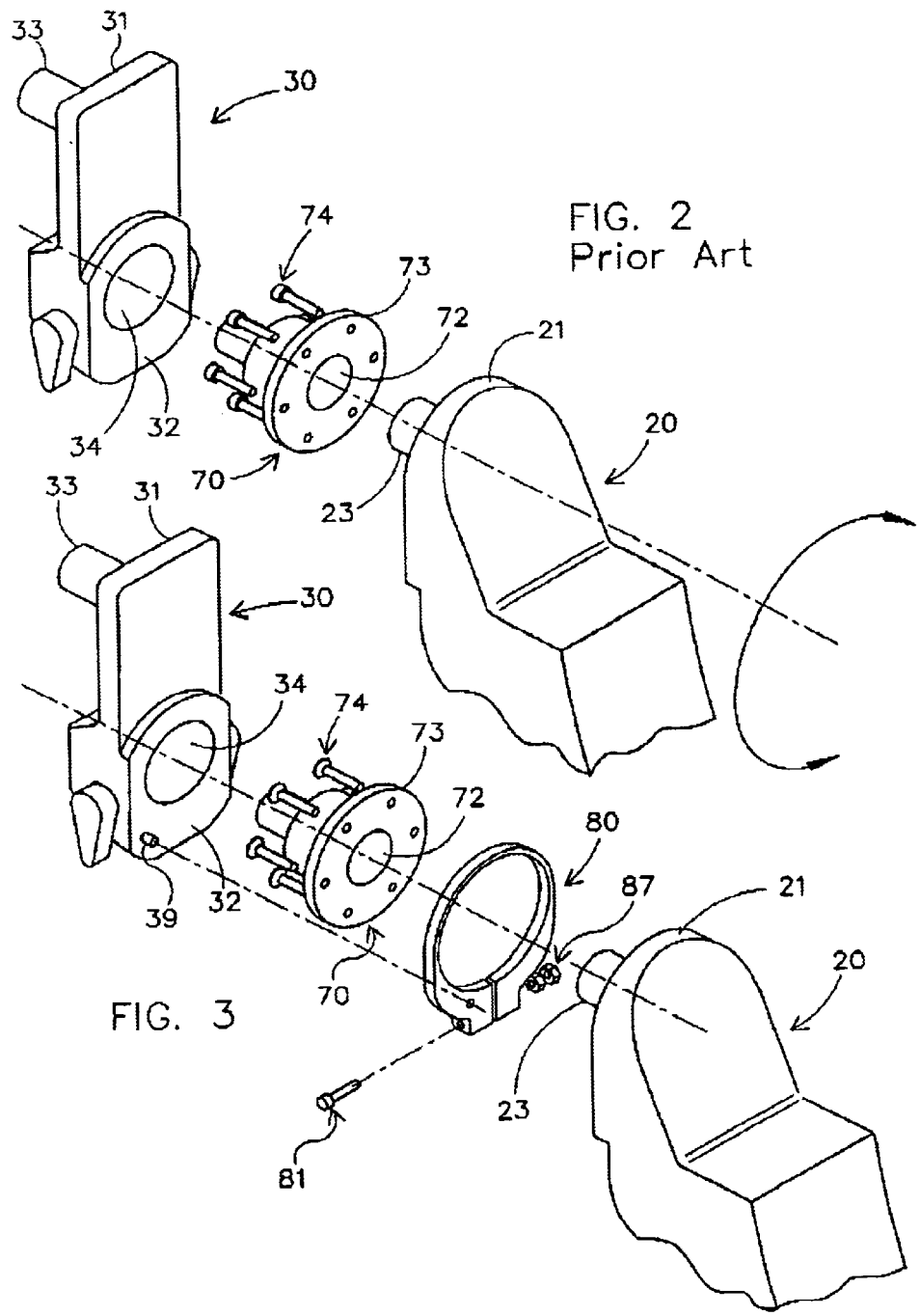
FIG. 2 is a top, front and left side exploded perspective view of a prior art yoke, sleeve, and support arm.
FIG. 3 is a top, front and left side exploded perspective view of the yoke, frictional brake element, sleeve and support arm as they are employed on a device of the present invention.

The yoke 20, as illustrated in FIGS. 2 and 3, has a first end 21 attached to the support arm 30 and a second end 22 attached to the C-arm 100. Since the C-arm 100 is an overhanging part, the strength of the yoke 20 and the safety of patients and healthcare workers is obviously a concern. In order to strengthen the yoke 20, the device of the present invention provides for a steel sleeve 70 to enclose the pin 23 at the first end 21 of the yoke 20.

As shown in greater detail in FIG. 4, the pin 23 on the first end 21 of the yoke 20 is generally cylindrical in shape. The sleeve 70 can be generally thought of as a cylinder having a first end 71 and a second open end 72 that slides snugly over the pin 23. The sleeve 70 is mounted to the aluminum yoke 20 using bolts 74, although other means of attachment are possible. The bolts 74 connect the skirt 73 of the sleeve 70 to the first end of the yoke 21 The sleeve 70 is also generally attached to the yoke 20 through the pin using a bolt 75 or other means of attachment.

Optimally, the center of gravity of the C-arm 100 is as close as possible to the rotation axis of the C-arm 100. As the center of gravity of the C-arm 100 gets closer to the axis of rotation, the C-arm's 100 natural tendency to "swing" is reduced. However, even if the center of gravity of the C-arm 100 is exactly at the axis of rotation, production variances will require the addition of some means for controlling this tendency to swing. The problem is frequently solved through use of a gas spring that counters the imbalance due to the eccentricity of the center of gravity. Unfortunately, the gas spring mechanism requirement lengthens the overall machine 10. In the field of orthopedic medicine, compact length and lower cost are more important than bringing the rotation axis of the C-arm 100 closer to the center of gravity.

The C-arm 100 includes a generally semicircular member 104 that is held in a rotational sliding position by a series of bearings (not shown) located on second end 22 of the yoke 20. The first end 101 of the C-arm 100 includes an x-ray source 12 and the second end 102 of the C-arm 100 includes an x-ray detector 14. The C-arm 100 maintains the x-ray source 12 and the image detector 14 in diametrically opposite, but facing, positions.

The C-arm 100 is generally capable of movement in at least two degrees of freedom. The first end of the yoke 20 is permitted to rotate 360 degrees about its connection to the support arm 30. Also, the exterior semicircular member 104 of the C-arm 100 is permitted to roll along the second end 22 of the yoke 20. Generally, the C-arm 100 is permitted to rotate orbitally around its own axis. The breadth of rotation of the C-arm 100 is limited only by the width of the yoke 20.

In order to counteract the rotation of the C-arm 100, a simple but effective means for preventing the C-arm 100 from swinging down rapidly was required. In the device of the present invention, a variable friction disc 80 is installed between the yoke 20 and the support assembly 30. The variable friction disc 80 is preferably constructed of aluminum bronze, or Hardalu, although other materials would be acceptable. Generally, the variable friction disc 80 surrounds the sleeve 70 and inhibits free rotation of the sleeve 70 with respect to the support arm 30. See FIGS. 3 and 4. The amount of friction provided by the friction ring 80 must be carefully calculated such that free rotation of the yoke 20 and C-arm 100 is inhibited but not made so difficult to rotate that it become onerous for one person to do so.

Figure 6:
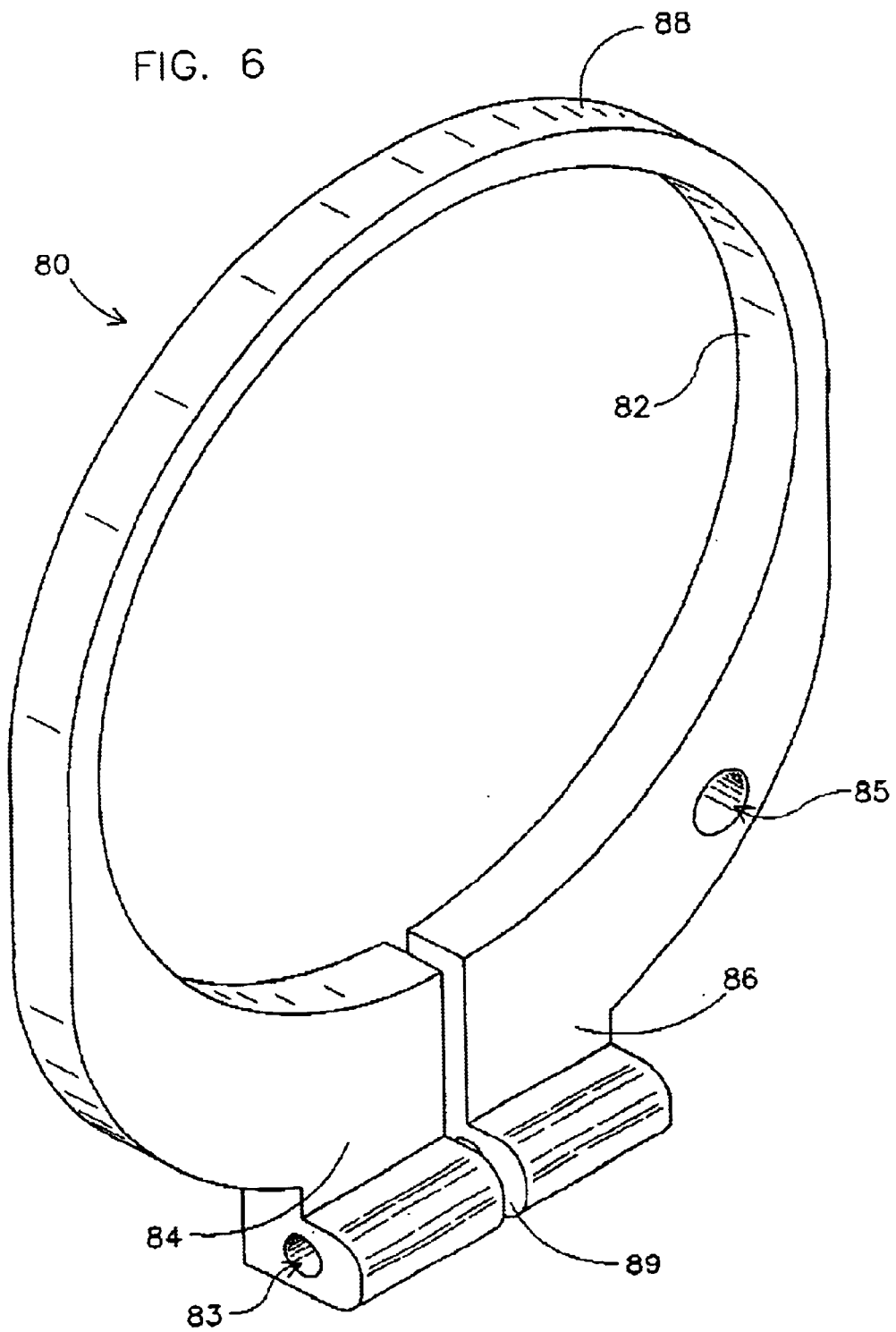
FIG. 6 is a top, front and left side perspective view of the frictional brake element constructed in accordance with the present invention.
Figure 7:
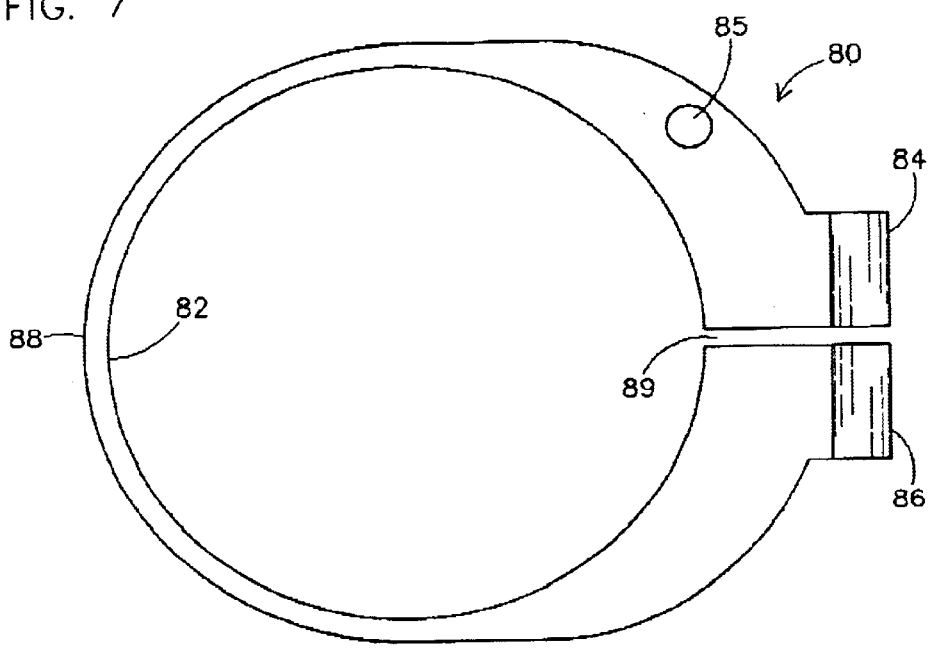
FIG. 7 is a front elevational view of the frictional brake element.
Figure 8:
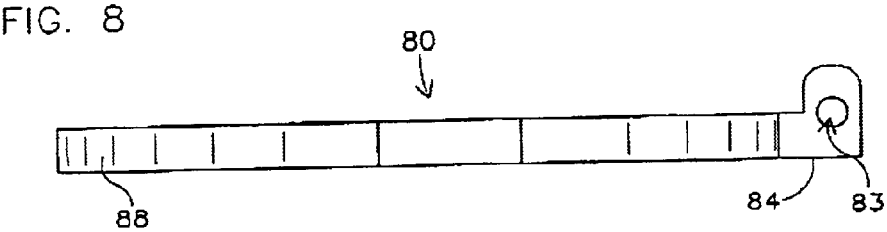
FIG. 8 is a left side elevational view of the frictional brake element.

Specifically, the friction ring 80 of the present invention fits around the sleeve 70 and is generally circular in shape. See FIGS. 5, 6 and 8. In a preferred embodiment, the friction ring 80 is fabricated generally in the shape of a of the second end 32 of the support arm 30 which in contacts. In other words, the friction ring 80 includes a generally circular inner surface 82, an upper band shaped portion 88, and first and second lower portions 84, 86. The lower portions 84, 86 of the ring 80 are separated by a vertically oriented ring opening or gap 89. Each lower portion 84, 86 includes a longitudinally extending aperture 83 that permits passage of a bolt 81 therethrough, thereby connecting one lower portion 84 of the ring 80 to the other lower portion of the ring 86. See FIG. 6. The threaded end of the bolt 81 is secured by one or more nuts 87 or other suitable fastening devices. The gap 89 of the frictional ring 80 provides some adjustability of the ring 80 in that the friction ring 80 has a screw adjustment 81, 87 that provides for tightening and loosening of the friction ring 80. The variable friction ring 80 is adjustable to accommodate variations in the size and weight of parts. Therefore, the device of the present invention offers greater manufacturing flexibility.

Generally, the friction ring 80 is also anchored in some manner so as to prevent relative rotation of it with respect to the support arm 30. Specifically, the support arm 30 provides a dowel pin 39 the same as or slightly lesser in length as the thickness of the frictional ring 80. The friction ring 80 has an aperture 85 to accommodate the dowel pin 39, such that, when installed, the friction ring 80 is not permitted to rotate.

It is to be understood that the invention is not limited to the embodiments set forth herein but that the invention may be carried out in other ways without departure from the spirit of this invention. Based on the foregoing, it is apparent that there has been provided a C-arm x-ray apparatus that is either optimally balanced or that requires little effort to rotate by incorporation of a unique friction brake, which brake requires relatively few parts and that can be easily manufactured; that increases the friction between the C-arm and the Yoke so as to improve rotational control of the C-arm when the brake is not applied; that provides such a device while not increasing the overall length of the C-arm machine, which increase would also decreases stability; and that provides for an adjustment of the brake mechanism without requiring disassembly of the C-arm.

What is claimed is:

1. An x-ray imaging apparatus comprising
   a mobile support base,
   a vertically extendable column attached to the support base,
   an extendable cross arm having a first end slidably attached to the vertically extendable column and a second end,
   a support arm having a first end attached to the second end of the cross arm and a second end having an aperture,
   a yoke having a first end with a cylindrical pin and a second end,
   a steel sleeve having an integrally formed circular skirt attached to the first end of the yoke and surrounding the cylindrical pin on the yoke,
   a variable friction disc interposed between the sleeve and the support arm,
   a C-arm attached to the yoke,
   an x-ray source, and
   an image receptor,
   wherein the image receptor and the x-ray source are mounted on opposing ends of the C-arm.

2. The x-ray imaging apparatus of claim 1 wherein the variable friction disc is a fabricated from an alloy of aluminum bronze.

3. The x-ray imaging apparatus of claim 1 wherein the variable friction disc is fabricated from a resilient and durable material.

4. The x-ray imaging apparatus of claim 1 wherein the variable friction disc has a means for adjusting the tension of the friction disc.

5. The x-ray imaging apparatus of claim 1 wherein the support arm has a dowel pin and the variable friction disc has an aperture fitting on to the dowel pin thereby preventing rotation of the variable friction ring with respect to the support arm.

6. The x-ray imaging apparatus of claim 1 wherein the variable friction disc is generally in the shape of a yoke with one area of variable friction disc being elongated and having a gap therethrough, the width of said gap being variably adjustable by providing an aperture through said elongated area and an adjustment bolt through the aperture such that when the bolt is tightened or loosened the size of the variable friction disc is varied.

7. An x-ray imaging, apparatus comprising
   a mobile support base,
   a vertically extendable column attached to the support base,
   an extendable cross arm having a first end slidably attached to the a vertically extendable column and a second end having a generally circular aperture,
   a yoke having a first end with a cylindrical pin and a second end.
   a steel sleeve having an integrally formed circular skirt attached to the first end of the yoke and surrounding the cylindrical pin on the yoke, a variable friction disc fabricated from an alloy of aluminum bronze interposed between the sleeve and the support arm, a C-arm attached to the yoke, an x-ray source, and an image receptor, wherein the image receptor and the x-ray source are mounted on opposing ends of the C-arm.

8. The x-ray imaging apparatus or claim 7 wherein the variable friction disc is fabricated from a lightweight, wear resistant alloy.

9. The x-ray imaging apparatus of claim 7 wherein the variable friction disc has a means for adjusting the tension of the friction disc.

10. The x-ray imaging apparatus or claim 7 wherein the support arm has a dowel pin and the variable friction disc has an aperture fitting on to the dowel pin thereby preventing rotation of the variable friction ring with respect to the support arm.

11. The x-ray imaging apparatus of claim 7 wherein the variable friction disc is generally in the shape of a yoke, one area of variable friction disc is elongated and has an gap therethrough, the variable friction disc is not a complete circle, said elongated portion providing an aperture for a bolt, said elongated area also providing a gap therethrough such that the when a bolt is inserted the relative size of the variable friction disc can be varied.

12. An x-ray imaging apparatus comprising a mobile support base, a vertically extendable column attached to the support base, an extendable cross arm having a first end slidably attached to the vertically extendable column and a second end having a generally circular aperture, a support arm having a first end attached to the second end of the cross arm and a second end having an aperture, a yoke having a first end with a cylindrical pin and a second end, a steel sleeve having an integrally formed circular skirt attached to the first end of the yoke and surrounding the cylindrical pin oil the yoke, a variable friction disc fabricated from an alloy of aluminum and bronze interposed between the sleeve and the support arm, a C-arm attached to the yoke, an x-ray source, an image receptor, wherein the image receptor and the x-ray source are mounted on opposing ends of the C-arm.

13. The x-ray imaging apparatus of claim 12 wherein the variable friction disc has a means for adjusting the tension of the frictional disc.

14. The x-ray imaging apparatus of claim 13 wherein the support arm has a dowel pin and the variable friction disc has an aperture fitting on to the dowel pin thereby preventing rotation of the variable friction ring with respect to the support arm.

15. The x-ray imaging apparatus of claim 14 wherein the variable friction disc is generally in the shape of a yoke with one area of variable friction disc being elongated and having a gap therethrough, the width of said gap being variably adjustable by providing an aperture through said elongated area and an adjustment bolt through the aperture such that when the bolt is tightened or loosened the size of the variable friction disc is varied.

16. An x-ray imaging apparatus comprising a mobile support base, a vertically extendable column attached to the support base, an extendable cross arm having a first end slidably attached to the vertically extendable column and a second end having a generally circular aperture, a support arm having a first end attached to the second end of the cross arm and a second end having an aperture, a yoke having a first end with a cylindrical pin and a second end, a steel sleeve having an integrally formed circular skirt attached to the first end of the yoke and surrounding the cylindrical pin on the yoke, a variable friction disc fabricated from a lightweight rigid material interposed between the sleeve and the second end of the support arm, means for adjusting tile tension of the variable friction disc, a C-arm attached to the yoke, an x-ray source, an image receptor, wherein the image receptor and the x-ray source are mounted on opposing ends of the C-arm.

17. The x-ray imaging apparatus of claim 16 wherein the support arm has a dowel pin and the variable friction disc has an aperture fitting on to the dowel pin thereby preventing rotation of the variable friction ring with respect to the support arm.

18. The x-ray imaging apparatus of claim 17 wherein the variable friction disc is generally in the shape of a yoke with one area of variable friction disc being elongated and having a gap therethrough, the width of said gap being variably adjustable by providing an aperture through said elongated area and an adjustment bolt through the aperture such that when the bolt is tightened or loosened the size of the variable friction disc is varied.

19. An x-ray imaging apparatus comprising a mobile support base, a vertically extendable column attached to the support base, an extendable cross arm having a first end slidably attached to the vertically extendable column and a second end having a generally circular aperture, a support arm having a first end attached to the second end of the cross arm and a second end having an aperture, a yoke having a first end with a cylindrical pin, a dowel pin mounted eccentrically from the cylindrical pin and a second end, a steel sleeve having an integrally formed circular skirt attached to the first end of the yoke and surrounding the cylindrical pin on tile yoke, a variable friction disc having an aperture generally the same size and shape of the dowel pin interposed between the sleeve and the second end of the support arm, wherein the variable friction disc is prohibited from rotating with respect to the support arm, means for adjusting the tension of the variable friction disc, a C-arm attached to the yoke, an x-ray source, an image receptor, wherein the image receptor and the x-ray source are mounted on opposing ends of the C-arm.

20. The x-ray imaging apparatus of claim 19 wherein the variable friction disc is generally in the shape of a yoke with one area of variable friction disc being elongated and having a gap therethrough, the width of said gap being variably adjustable by providing an aperture through said elongated area and an adjustment bolt through the aperture such that when the bolt is tightened or loosened the size of the variable friction disc is varied.

* * * * *

UNITED STATES PATENT AND TRADEMARK OFFICE
CERTIFICATE OF CORRECTION

PATENT NO. : 6,733,177 B2
DATED : May 11, 2004
INVENTOR(S) : Pillai et al.

It is certified that error appears in the above-identified patent and that said Letters Patent is hereby corrected as shown below:

Column 6,
Line 61, please delete the first instance of "a";

Column 7,
Line 9, please delete "or" and insert -- of --;
Line 43, please delete "oll" and insert -- on --;

Column 8,
Line 19, please delete "tile" and insert -- the --;
Line 55, please delete "tile" and insert -- the --.

Signed and Sealed this

Thirtieth Day of November, 2004

JON W. DUDAS
*Director of the United States Patent and Trademark Office*